United States Patent [19]

Huber

[11] Patent Number: 5,026,652
[45] Date of Patent: Jun. 25, 1991

[54] METHOD AND DEVICE FOR MERCURY ANALYSIS

[75] Inventor: Bernhard Huber, Überlingen, Fed. Rep. of Germany

[73] Assignee: Bodenseekwerk Perkin Elmer GmbH, Überlingen, Fed. Rep. of Germany

[21] Appl. No.: 399,801

[22] Filed: Aug. 29, 1989

[30] Foreign Application Priority Data

Sep. 8, 1988 [DE] Fed. Rep. of Germany ....... 3830504

[51] Int. Cl.$^5$ ...................... G01N 21/00; G01N 25/00
[52] U.S. Cl. ..................................... 436/81; 436/171; 422/80; 356/36
[58] Field of Search ..................... 436/81, 171; 356/86, 356/311, 312; 422/78, 80, 91

[56] References Cited

U.S. PATENT DOCUMENTS 3,852,604 12/1974 Grengg ............................. 250/373
4,023,929 5/1977 Becker et al. ................. 23/230 PC Primary Examiner—David L. Lacey
Assistant Examiner—David Redding
Attorney, Agent, or Firm—Thomas P. Murphy; Edwin T. Grimes

[57] ABSTRACT

An apparatus and method for analyzing mercury by the atomic absorption spectrometry technique consisting of a quartz collecting tube containing a metallic net for collecting an amalgam of mercury sample, a heater for heating the collecting tube sufficiently to convert the mercury sample to an atomic state for appropriate analysis at another location, and a fluid cooling device for quickly cooling the collecting tube and metallic net to thereby prepare for the next sample analysis. The collecting tube is positioned and arranged such that in a first position it is inside of the heater and quickly after conversion of the mercury sample the tube is moved to a second position outside of the heater and adjacent to the cooling device.

2 Claims, 1 Drawing Sheet

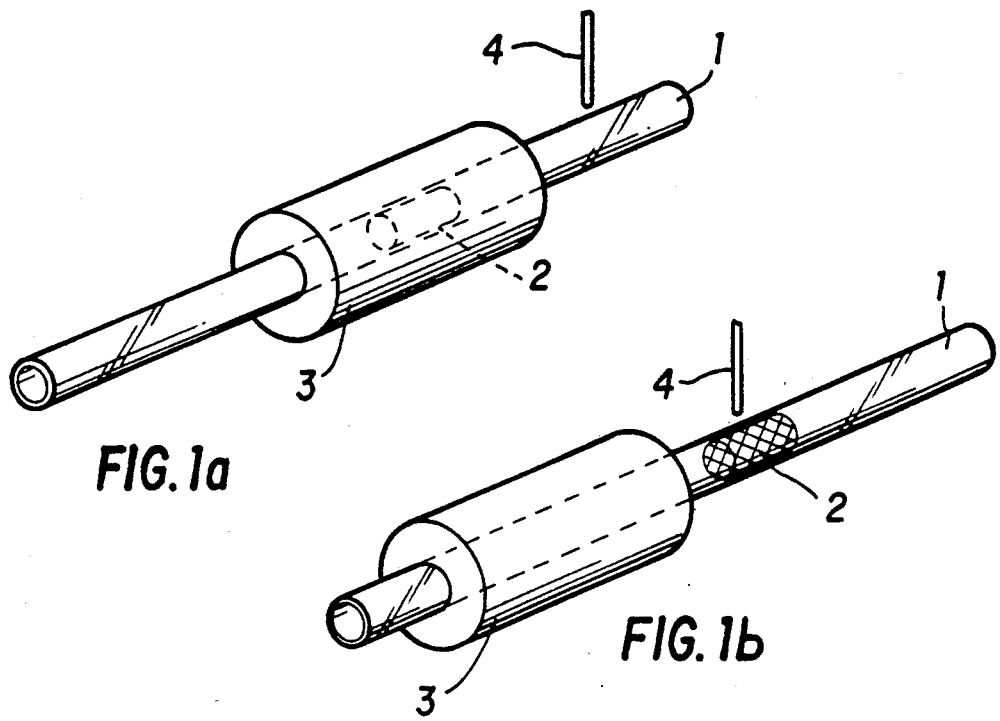
FIG. 1a
FIG. 1b
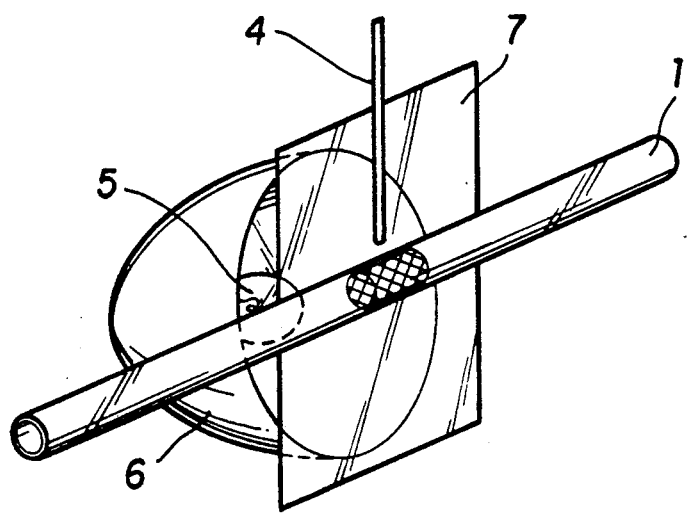
FIG. 2

METHOD AND DEVICE FOR MERCURY ANALYSIS

BACKGROUND OF THE INVENTION

In the atomic absorption spectrometry (AAS) it is common to reduce the mercury (Hg) to metal by suitable chemical agents (e.g. sodium hydroboron). The vapor pressure of the mercury at an ambient temperature is already high enough so that the mercury can be passed into a measuring cuvette by a gas flow.

The sensitivity of this method can be considerably increased when the generated mercury vapor is guide through finely distribute metal net (e.g., gold) which metal is then heated. The mercury accumulates at the metal as an amalgan and can be abruptly release by heating so that a higher Hg-density is generated in the measuring cuvette of the spectrometer. Thereby, the sensitivity of the prior devices is increased by approximately factor 10.

Prior devices of this type use a quartz tube with an inner diameter of about 4mm for accommodating the gold net. The gold net is cut to a width of approximately 6mm, and is rolled up and inserted into the quartz tube. The tube with the gold net is arranged in a wire coil which can be electrically heated to approximately 600° C.

When the analysis takes place, the reducing agent is added to the sample, a gas flow is passed through the sample and then through the (cold) quartz tube with the gold net. When the reaction has finished, the quartz tube with the gold net is heated whereby the mercury is abruptly released and is passed into the measuring cuvette.

Now, it is disadvantageous that after the analysis is conducted, a waiting period is needed until the coil, the quartz tube and the gold net have again reached an ambient temperature since a generation of amalgam is only possible at relatively low temperatures.

It is the object of the invention to reduce the length of this waiting period and to provide a faster, better defined temperature increase.

BRIEF DESCRIPTION OF THE INVENTION

The present invention relates to an apparatus and method of analyzing mercury according to the atomic absorption spectrometry technique. According to the present invention the speed at which successive samples can be analyzed can be greatly increased by quickly cooling the site where the mercury sample is heated to the atomic state so that another sample can be quickly introduced without vaporization. In carrying out the present invention a quartz tube has a gold net which collects a mercury amalgan. Heater means adjacent the sample area then heats the mercury sample to release it to the atomic state for analysis. Once the sample is removed from the tube the tube and net are quickly cooled so that another sample may be introduced without a disturbing effect. The cooling means may be a gas or liquid. The heater may be a furnace or a lamp with an enhancing mirror. A transparent plate may be placed between the lamp and sample tube to protect the lamp from damage. Where the heater is an enclosing furnace the tube is movable to be able to place the sample near the cooling means. Where a heat lamp is used the cooling means may be positioned such that the sample tube need not be movable.

BRIEF DESCRIPTION OF THE DRAWINGS

FIGS. 1a and 1b are a pictorial representation of a first embodiment of the present invention; and FIG. 2 is a pictorial representation of a second embodiment of the present invention.

DESCRIPTION OF THE INVENTION

FIG. 1 illustrates one possibility. The quartz tube (1) with the gold net (2) is movably arranged within a small furnace (3). The temperature of this furnace (3) can be controlled. Next to the furnace (3) a nozzle (4) is provided. By this nozzle (4) a cooling agent can be blown on the quartz tube (1).

For collecting purposes, the quartz tube (1) is positioned such that the gold net (2) is below the nozzle (4). For heating-out purposes, the quartz tube (1) is moved such that the gold net (2) is arranged in the furnace (3). This furnace (3) is continuously heated to a temperature of 600° C., for example. So the gold net (2) is heated within a very short period of time to a defined temperature. When the heating-out has been finished, the tube (1) is again moved to the "collecting" position. By the nozzle (4) the tube (1) can be quickly recooled.

A further possibility is illustrated by FIG. 2. Here the quartz tube (1) is stationary. If required, the quartz tube (1) is heated by one (or several) lamps (5) ad a concave mirror (6). Such a combination (lamp with concave mirror) can be bought ready-made. (Osram Halogen Bellaphot). A protecting pane (7) can be arranged between the lamp (5) and the quartz tube (1). This protecting pane (7) allows the cooling of the quartz tube (1) through the nozzle (4) with a liquid, without exposing the lamp (5) to risk.

When the mercury is collected the lamp (5) is switched off. For heating-out the lamp (5) is switched on. The concave mirror (6) onto the gold net (2) which thereby is heated up. The protecting pane (7) and the quartz tube (1) are to a large degree transparent to the radiation of the lamp (5). (Infrared). When, after heating-out, the lamp (5) is again switched off the quartz tube (1) can be quickly cooled down with a gas or liquid flow through the nozzle (4).

What is claimed is:

1. A method of mercury analysis comprising the steps of:
   introducing a mercury sample reacted with a reducing agent into a collection tube having a metallic net for collecting mercury thereon,
   heating the collection tube and metallic net so as to abruptly release the mercury collected on the metallic net in an atomic state, said step of heating the collection tube and metallic net comprising heating the collection tube and metallic net in a furnace,
   passing the mercury in atomic state into a measuring cuvette for analysis, and
   quickly cooling the collection tube and metallic net by fluid flow for introduction of a further mercury sample, said step of quickly cooling the collection tube and metallic net comprising removing the collection tube and metallic net from said furnace and subjecting it to a cooling fluid flow.

2. A device for use in mercury analysis in atomic absorption spectroscopy comprising
   a furnace, means for heating a collecting tube means to a temperature that causes the abrupt release of mercury in an atomic state fluid cooling means disposed exteriorly of said furnace,
said collecting tube means having a metallic net for collecting mercury thereon from a mercury sample reacted with a reducing agent, said collecting tube means being positioned and arranged so as to be movable between a first position within said furnace means wherein it is heated to a temperature to abruptly release mercury collected on said metallic net in an atomic state and a second position outside of said furnace means adjacent said fluid cooling means for quickly cooling said collecting tube means and metallic net to a temperature for collecting mercury thereon.

* * * * *